United States Patent [19]

Hirose et al.

[11] Patent Number: 5,436,006
[45] Date of Patent: Jul. 25, 1995

[54] SYNTHETIC OIL AND COSMETICS AND EXTERNAL PREPARATIONS CONTAINING THE SAME

[75] Inventors: Tadashiro Hirose; Yoshihiro Ueda; Takashi Murata, all of Kanagawa, Japan

[73] Assignee: The Nisshin Oil Mills, Ltd., Tokyo, Japan

[21] Appl. No.: 95,199

[22] Filed: Jul. 23, 1993

[30] Foreign Application Priority Data

Jul. 27, 1992 [JP] Japan ................................. 4-219759
May 17, 1993 [JP] Japan ................................. 5-139021

[51] Int. Cl.⁶ ..................... A61K 7/48; A61K 7/027; C11C 3/02
[52] U.S. Cl. ..................... 424/401; 424/49; 424/64; 424/70.1; 424/402; 424/436; 424/484; 424/70.11; 514/552; 514/844; 514/846; 514/873; 514/937; 554/161; 554/168; 554/173; 554/174
[58] Field of Search ............... 424/401, 402, 484, 64, 424/552, 49, 70, 436; 514/786, 844, 846, 873, 937; 554/161, 168, 173, 174

[56] References Cited

U.S. PATENT DOCUMENTS 4,868,220 9/1989 Scheuffgen ...................... 514/784

FOREIGN PATENT DOCUMENTS 27447 of 1976 Japan .
66637 of 1977 Japan .
45373 of 1978 Japan .
7168 of 1986 Japan .
7403 of 1986 Japan .

OTHER PUBLICATIONS

CA registry (1994), Montanic Aud.

*Primary Examiner*—Jyothsna Venkat
*Attorney, Agent, or Firm*—Oblon, Spivak, McClelland, Maier & Neustadt

[57] ABSTRACT

Diclosed is a lanolin-like synthetic oil produced by esterification of glycerol with a branched fatty acid having 6 to 14 carbon atoms, a linear fatty acid having 15 to 28 carbon atoms and a dibasic acid having 4 to 10 carbon atoms while all the following conditions (a) to (c) are satisfied:

(a) molar ratio of the branched fatty acid to the linear fatty acid ranges from 1.7 to 2.3,
(b) 0.7 to 0.8 mol of the dibasic acid is used per mol of glycerol, and
(c) the number of remaining hydroxyl group ranges from 0.4 to 0.6 for three hydroxyl groups of glycerol.

The synthetic ester oil has a color, smell and stability superior to those of lanolin and an adherability, spreadability, gloss and touch very similar to those of lanolin. Such an oil can be suitably incorporated into cosmetics, toiletries and external preparations to overcome the defects of lanolin and also to exhibit the characteristic features of the oil.

3 Claims, No Drawings

SYNTHETIC OIL AND COSMETICS AND EXTERNAL PREPARATIONS CONTAINING THE SAME

BACKGROUND OF THE INVENTION

The present invention relates to a new synthetic ester oil usable as a substitute for lanolin, as well as cosmetics, toiletries and external preparations including drugs and quasi-drugs containing it.

Lanolin is incorporated into various cosmetics and toiletries and used as a base for ointments in virtue of its excellent properties such as adherability, wettability and emulsifiability. However, it was often pointed out that lanolin has a color and smell peculiar to animal oils and fats and it also has defects due to complicated substances contained therein and unstable quality thereof. Although lanolin recently available on the market has a high purity, since it is purified by a purification process comprising various steps, the essential defects thereof still remain. Further the use of lanolin tends to be indirectly controlled by recent worldwide tendency to prevention of cruelty to animals and conservation of nature.

Under these circumstances, investigations were heretofore made for the purpose of developing a substance similar to lanolin or usable as a substitute for lanolin. For example, Japanese Patent Publication for Opposition Purpurse (hereinafter referred to as "J. P. KOKOKU") Nos. Sho 61-7168 and Sho 61-7403 propose esterifcation products prepared from a polyhydric alcohol such as glycerol, diglycerol, trimethylolpropane, pentaerythritol or sorbitol and a monobasic acid having 8 to 22 carbon atoms or dibasic acid having 12 to 20 carbon atoms as substances having characteristics similar to those of lanolin and vaseline. Further Japanese Patent Unexamined Published Application (hereinafter referred to as "J. P. KOKAI") No. Sho 58-198565 propoes equimolar mixed esters such as pentaerythritol/dicoconut fatty acid ester and di-octadecyl citrate, as well as a mixture of oleic acid monodiglyceride, palmitic acid and/or stearic acid mono-diglyceride and ethylene oxide-added vegetable sterol as substitutes for wool wax.

However, the lanolin-like substances or substitutes for lanolin heretofore proposed were inferior to lanolin, since they are heavy to the touch and have insuffucient spreadability and adherability and the constituents are separated out during storage. This fact indicates that a substitute for lanolin cannot be easily chemically synthesized, since lanolin is a natural product having an extremely complicated composition containing minor constituents peculiar to the natural oils and fats such as esters of short to long, linear and branched, saturated and unsaturated carboxylic acids, hydroxy acids, dicarboxylic acids, etc. with cholesterol, lanosterol, etc. In other words, development of an oil-like substance having the characteristics of lanolin but free from the defects thereof or development of stable cosmetics, toiletries and external preparations such as drugs and quasi-drugs containing it has been demanded.

SUMMARY OF THE INVENTION

A primary object of the present invention is to provide a synthetic oil superior to lanolin in color, smell and stability and having properties such as adhesive properties, spreadability, gloss and touch similar to those of lanolin.

Another object of the present invention is to provide cosmetics, toiletries and external preparations such as drugs and quasi-drugs containing the synthetic oil.

These and other objects of the present invention will be apparent from the following description and Examples.

The development of the synthetic oil of the present invention has been completed on the basis of a finding that only an esterification product of fatty acids including a branched fatty acid having a medium chain length, long-chain linear fatty acid and dibasic acid having a medium chain length with a polyhydric alcohol in a specified proportion has properties extremely similar to those of lanolin and is free from the above-described defects.

Therefore, the synthetic oil of the present invention is a lanolin-like synthetic oil produced by esterification of glycerol with a branched fatty acid having medium chain length, a long-chain linear fatty acid and a dibasic acid having medium chain length while all the following conditions (a) to (c) are satisfied:

(a) molar ratio of the branched fatty acid having a medium chain length to the long-chain linear fatty acid ranges from 1.7 to 2.3, (b) 0.7 to 0.8 mol of the dibasic acid having a medium chain length is used per mol of glycerol, and (c) the number of remaining hydroxyl group ranges 0.4 to 0.6 for three hydroxyl groups of glycerol.

DESCRIPTION OF THE PREFERRED EMBODIMENTS

The branched fatty acids having medium chain length used as a starting material for the synthetic oil of the present invention are saturated fatty acids having preferably 6 to 14 carbon atoms, more preferably 8 to 12 carbon atoms, such as 2-ethylhexanoic acid, isooctylic acid, isononanoic acid, isodecanoic acid and neo-tridecanoic acid. In this connection, it is preferable that the branched fatty acids have an alkyl branch of 1 to 3 carbon atoms, more preferably 1 to 2 carbon atoms. The long-chain fatty acids are those having preferably 15 to 28 carbon atoms, more preferably 18 to 28 carbon atoms, such as palmitic acid, stearic acid, behenic acid, montanic acid, oleic acid and erucic acid, most preferably 18 to 22 carbon atoms. Among these, saturated one is preferred. The dibasic acids having medium chain length are those having preferably 4 to 10 carbon atoms, more preferably 6 to 10 carbon atoms, such as adipic acid, succinic acid, pimelic acid, azelaic acid and sebacic acid. Among these, saturated one is preferred. These examples by no means limit the starting materials for the synthetic oils of the present invention. The respective kinds of the fatty acids can be used either singly or in combination of two or more of them.

The esterification reaction is conducted by an ordinary method in the presence or absence of a catalyst under atmospheric or reduced pressure. After completion of the esterification reaction, the reaction mixture is, if necessary, purified by decoloration with a decolorant followed by deodorization to obtain the esterification product of the present invention. Such an esterification product having an acid value of below 1 or around 1 after the purification has a high degree of purification and the proportion of the constituents of its composition is very close to the proportion of the starting compounds used. This product is a lanolin-like, viscous paste and when it is applied to hands, its adherability, gloss, spreadability and touch are very similar to those of lanolin. These characteristic properties cannot be obtained when any of the combination of the branched fatty acid having medium chain length, long-chain linear fatty acid, dibasic acid having medium chain length and glycerol and the above-described conditions is not satisfied.

In the present invention, the varieties and proportions of the fatty acids and dibasic acid used as the starting materials in the esterification step are particularly important, and they are the characteristic features of the present invention. The detailed description will be made on this point.

Table 1 shows a part of the results obtained after investigation of the combination and proportion of the starting materials for completing the synhthetic oil of the present invention.

TABLE 1

| Sample | L-1 | L-2 | L-3 | L-4 |
|---|---|---|---|---|
| Starting materials for esters and proportion thereof | | | | |
| Synthesis Ex. | 5 | 6 | 7 | 1 |
| Starting material amount (mol) | glycerol (1.0) | | | |
| | isooctylic acid (1.0) | isononanoic acid (1.0) | isononanoic acid (0.5) | isononanoic acid (0.7) |
| | stearic acid (0.6) | stearic acid (0.5) | stearic acid (0.6) | behenic acid (0.3) |
| | adipic acid (0.5) | sebacid acid (0.7) | sebacic acid (0.7) | sebacic acid (0.7) |
| Blending condition | | | | |
| (a) Note (1) | 1.7 | 2.0 | 0.8 | 2.3 |
| (b) Note (2) | 0.5 | 0.7 | 0.7 | 0.7 |
| (c) Note (3) | 0.4 | 0.1 | 0.5 | 0.6 |
| Sample | L-5 | L-6 | L-7 | M-1 |
| Synthesis Ex. | 2 | 3 | 4 | 8 |
| Starting material amount (mol) | glycerol (1.0) | | | |
| | isooctylic acid (0.6) | isooctylic acid (0.6) | isononanoic acid (0.76) | isostearic acid (0.7) |
| | stearic acid (0.3) | montanic acid (0.3) | myristic acid (0.44) | stearic acid (0.3) |
| | adipic acid (0.8) | succinic acid (0.8) | adipic acid (0.7) | sebacic acid (0.7) |
| Blending condition | | | | |
| (a) Note (1) | 2.0 | 2.0 | 1.7 | 2.3 |
| (b) Note (2) | 0.8 | 0.8 | 0.7 | 0.7 |
| (c) Note (3) | 0.5 | 0.5 | 0.4 | 0.6 |

Notes:
(1) Molar ratio of branched fatty acid having medium chain length to long chain linear fatty acid.
(2) Amount (unit: mol) of dibasic acid having medium chain length per mol of glycerol, and
(3) Average number of remaining hydroxyl group for 3 hydroxyl groups of glycerol.

Sample L-1 given in Table 1 had adherability, spreadability and touch which were all lower than those of lanolin. Sample L-2 scarcely had the adherability like that of a thick syrup which is peculiar to lanolin. When the long-chain linear fatty acid and the branched fatty acid having medium chain length were contained in substantially equimolar amounts as in sample L-3, the touch of the sample becomes as hard as wax. On the contrary, when Sample L-4 was applied to hands, the adherability, gloss and spreadability thereof were very similar to those of lanolin and, in addition, the touch of Sample L-4 was also similar to that of lanolin. This inclination was observed when sample L-5, L-6 or L-7 was used. The characteristic adherability, spreadability and touch of M-1 containing isostearic acid (a long-chain branched fatty acid) in place of the branched fatty acid having medium length were not so remarkable. It is apparent from these results that the indispensable conditions for the ester oils having a touch and properties very similar to those of lanolin are that they are esterification products of glycerol with a branched fatty acid having a medium chain length, a long-chain linear fatty acid and a dibasic acid having a medium chain length and that they satisfy all of the following conditions:

(a) molar ratio of the branched fatty acid having a medium chain length to the long-chain linear fatty acid ranges from 1.7 to 2.3,
(b) 0.7 to 0.8 mol of the dibasic acid having a medium chain length is used per mol of glycerol, and
(c) the number of hydroxyl group remaining in the esterification product ranges from 0.4 to 0.6 for three hydroxyl groups of glycerol. The lanolin-like synthetic oil intended in the present invention cannot be obtained unless all of these conditions are satisfied.

The synthetic oil of the present invention thus obtained is usable in place of a part or the whole of lanolin or lanolin-like substances heretofore used in the preparation of cosmetics, toiletries, drugs such as ointments and quasi-drugs. Since the starting materials can be suitably selected within the above-specified conditions, the touch and properties of the oil and products containing the oil can be controlled depending on the conditions and circumstances under which they are used. It is an advantage of the present invention. The synthetic oil of the present invention can be incorporated into known cosmetics which contained lanolin or an oil component having a function similar to that of lanolin. The cosmetics are not particularly limited and include, for example, creams, emulsions, lotions, lipsticks and foundation creams. The toiletries are also not particularly limited and they include, for example, shampoos, hair treatments and bath liquids. Examples of the external preparations include drugs such as ointments, plasters, poultices and suppositories, and quasi-drugs such as hair tonics, hair growers and dentifrices. The synthetic oil of the present invention can be incorporated into these preparations in an amount of usually 0.1 to 50% by weight, preferably 1 to 30% by weight. When it is used in an amount over this range, the effect of realizing the intended properties cannot be obtained and the hardness cannot be kept depending on the product.

These products can be produced from the synthetic oil of the present invention and other known components by an ordinary method. Namely, the products are produced by suitably combining the oil of the present invention with components selected from among oily substances such as olive oil, lard, cacao butter, isopropyl myristate, silicone, bees wax, vaseline, liquid paraffin, waxes, higher fatty acids and higher alcohols; surfactants such as emulsifiers, dispersants and solubilizers; perfumes; pigments; viscosity modifiers such as thickening agents; monohydric and polyhydric alcohols; aqueous components such as humectants, pH adjustors and antiseptics; powdery components such as kaolin and talc; medical components such as vitamins, hormones, antibiotics, antimicrobial substances, antiinflammatory agents, sedatives and antipruritic drugs; drug absorption-accelerators; and purified water, and then mixing, blending, dispersing, emulsifying and/or dissolving them under heating or without heating to form a liquid, paste, gel, semi-solid or solid. The product thus obtained is applied to the skin, hair or body hair either directly or indirectly with a gauze, lint, piece of paper or the like.

The present invention is illustrated by the following synthesis Examples and Examples.

Synthesis Example 1

92.1 g (1 mol) of glycerol (product of Kao Corporation), 101 g (0.7 mol) of isononanoic acid (product of Nissan Chemical Industries, Ltd.), 102 g (0.3 mol) of behenic acid (product of New Japan Chemical Co., Ltd.) and 142 g (0.7 mol) of sebasic acid (product of Ogura Gosei Co., Ltd.) were fed into a 1l four-necked flask. 0.05% by weight, based on the mixture, of p-toluenesulfonic acid as the catalyst was added thereto. The resultant mixture was stirred at 120° to 200° C. for 15 hours in nitrogen gas atmosphere to conduct the esterification reaction by an ordinary method. The esterification reaction product was decolored with activated clay by an ordinary method and then deodorized under reduced pressure. The resultant esterification product (sample L-4) had an acid value of 0.6, saponification value of 318 and hydroxyl value of 78.

Synthesis Examples 2 to 8

Esterification products (L-5, L-6, L-7, L-1, L-2, L-3 and were obtained in the same manner as that of Synthetic Example 1 except that the starting materials listed in Table 1 were used in a proportion given in Table 1. The resultant esterification products each had an acid value of not higher than 1 and the saponification value and hydroxyl value of each of them were substantially equal to those calculated from the amount of the starting materials used.

Example 1

The heat resistance tests of the esterification products (L-4, L-5, L-6 and L-7) of the present invention obtained in Synthesis Examples 1, 2 and 3 were conducted to obtain the results given in Table 2.

A purified lanolin on the market which was used in this test very weakly smelled an unpleasant odor peculiar to lanolin already in the initial stage of the experiment and its bad smell became loud after 8 hours. On the contrary, the esters L-4, L-5, L-6 and L-7 of the present invention were odorless in the initial stage of the experiment and they faintly smelled of an odor of deteriorated esters after 15 hours.

TABLE 2

| Sample | Heat resistance of esterification products | | | |
|---|---|---|---|---|
| | Start | After 1 h | After 3 h | After 10 h |
| Lanolin | Faint smell | Faint smell | Bad smell | Bad smell |
| L-4 | Odorless | Odorless | Odorless | Faint smell |
| L-5 | Odorless | Odorless | Odorless | Faint smell |
| L-6 | Odorless | Odorless | Odorless | Faint smell |
| L-7 | Odorless | Odorless | Odorless | Faint smell |

(Note)
The samples were kept at 80° C. in a constant temperature bath to examine whether or not they smelled. Lanolin used was purified lanolin on the market.

Example 2

The properties (adherability, spreadability and gloss) of the esterification products (L-4, L-5, L-6 and L-7) of the present invention and comparative esterification products (L-1, L-2, L-3 and M-1 obtained in Synthesis Examples 3 to 6, respectively and typical examples of esterification products known from J. P. KOKOKU No. Sho 51-27447, J. P. KOKAI No. Sho 52-66637 and J. P. KOKOKU Nos. Sho 61-7168, 61-7203 and 53-45373 esterified in the same manner as that of Synthesis Example 1) were organoleptically evaluated by 15 panelists (Table 3).

The products N-1 to N-5 are as follows:

- N-1: esterification product of glycerol (1.0 mol), stearic acid (2.4 mol) and sebacic acid (0.3 mol) as disclosed in J. P. KOKOKU No. 51-27447.
- N-2: esterification product of glycerol (1.0 mol), stearic acid (0.6 mol), isostearic acid (0.6 mol) and adipic acid (0.7 mol) as disclosed in J. P. KOKAI No. 52-66637.
- N-3: esterification product of diglycerol (1.0 mol), stearic acid (0.3 mol), isooctylic acid (0.3 mol) and eicosanedioic acid (1.0 mol) as disclosed in J. P. KOKOKU No. 61-7168.
- N-4: esterification product of glycerol (1.0 mol), isostearic acid (1.0 mol) and eicosanedioic acid (0.7 mol) as disclosed in J. P. KOKOKU No. 61-7203, and
- N-5: esterification product of stearic acid monoglyceride (1.0 mol), isooctylic acid (1.0 mol) and sebasic acid (0.5 mol) as disclosed in J. P. KOKOKU No. 53-25373.

TABLE 3

| | Properties of esterification products | | | | |
|---|---|---|---|---|---|
| | Sample | Adherability | Spreadability | Gloss | Total evaluation |
| Present invnetion | L-4 | 4.3 | 4.6 | 4.7 | 4.4 |
| | L-5 | 4.5 | 4.2 | 4.5 | 4.5 |
| | L-6 | 4.3 | 4.0 | 4.1 | 4.1 |
| | L-7 | 4.4 | 4.2 | 4.5 | 4.4 |
| Comparative example | L-1 | 3.0 | 2.8 | 3.5 | 3.2 |
| | L-2 | 2.2 | 3.5 | 4.0 | 3.5 |
| | L-3 | 3.0 | 2.5 | 3.8 | 3.3 |
| | M-1 | 2.3 | 3.2 | 3.3 | 3.1 |
| | N-1 | Evaluation was impossible, since it was solid | | | |
| | N-2 | 2.1 | 3.8 | 2.7 | 3.0 |
| | N-3 | 4.2 | 2.5 | 3.1 | 3.1 |
| | N-4 | 3.1 | 3.2 | 2.5 | 3.5 |
| | N-5 | 2.5 | 2.8 | 3.2 | 2.7 |

*The adherability, spreadability, gloss and total evaluation were each the average of the evaluation results classified into the following five ranks:
5: extremely close to lanolin.
4: quite close to lanolin.
3: slightly different from lanolin.
2: quite different from lanolin. and
1: utterly different from lanolin.

It was confirmed from the results that the esterification products of the present invention were excellent lanolin-like oils.

Example 3

Creams containing the esterification product (L-4) of the present invention or lanolin were prepared by an ordinary method. The feeling realized during the application of them and the touch realized after the application of them were evaluated in comparison with each other by 15 panelists. The cream containing lanolin will be referred to as cream A and that containing the esterification product (L-4) of the present invention will be referred to as cream B. The formulations of the creams are given in Table 4 and the results of the evaluation are given in Table 5. Table 5 shows the results of the evaluation of cream B as compared with those of cream A. Most of the 15 panelists concluded that cream B containing the esterification product of the present invention was equivalent to lanolin-containing cream A.

TABLE 4

| Formulation of cream | |
|---|---|
| Starting material | Amount (% by wt.) |
| Stearic acid | 3.0 |
| Cetanol | 3.0 |
| Octyldodecanol | 6.0 |
| Squalane | 2.0 |
| Liquid paraffin | 4.0 |
| Lanolin or L-4 | 4.0 |
| Glycerol | 8.0 |
| Polyoxyethylene sorbitan monostearate | 1.0 |
| Stearic acid monoglyceride | 3.0 |
| Methylparaben | 0.2 |
| Propylparaben | 0.1 |
| Tocopherol | 0.2 |
| Purified water | 65.5 |
| Total | 100.0 |

TABLE 5

| | Evaluation of cream | | | | | |
|---|---|---|---|---|---|---|
| | Feeling during application | | | Touch after application | | |
| | Superior | Equal | Inferior | Superior | Equal | Inferior |
| Number of panelists | 2 | 13 | 0 | 3 | 11 | 1 |

(Note)
Cream B (containing L-4 of the present invention) was evaluated in comparison with cream A (containing lanolin).

Example 4

Lipsticks containing the esterification product (L-5) of the present invention or lanolin were prepared by an ordinary method. The feeling realized during the application of them and the touch and gloss realized after the application of them were evaluated in comparison with each other in the same manner as that of Example 3. The lipstick containing lanolin will be referred to as lipstick A and that containing the esterification product (L-5) of the present invention will be referred to as lipstick B. The formulations of the lipsticks are given in Table 6 and the results of the evaluation are given in Table 7. Table 7 shows the results of the evaluation of lipstick B as compared with those of lipstick A. It was concluded that lipstick B containing the esterification product of the present invention was equivalent to lanolin-containing lipstick A like in the test of the creams.

TABLE 6

| Starting material | Amount (% by wt.) |
|---|---|
| Pigment and dye | 11.0 |
| Diisostearyl malate | 16.0 |
| Mica titanium | 3.0 |
| Diglyceryl triisostearate | 16.0 |
| Liquid paraffin | 16.0 |
| Lanolin or L-5 | 24.0 |
| Candelilla wax | 7.0 |
| Ceresine | 6.9 |
| Tocopherol | 0.1 |
| Total | 100.0 |

TABLE 7

| | Evaluation of lipstick | | | | | |
|---|---|---|---|---|---|---|
| | Feeling during application | | | Touch and gloss after application | | |
| | Superior | Equal | Inferior | Superior | Equal | Inferior |
| Number of panelists | 1 | 14 | 0 | 2 | 12 | 1 |

(Note)
Lipstick B (containing L-5 of the present invention) was evaluated in comparison with lipstick A (containing lanolin) by 15 panelists.

Example 5

Ointments containing the esterification product (L-4) of the present invention or lanolin were prepared by an ordinary method. The feeling realized during the application of them and the touch realized after the application of them were evaluated in comparison with each other in the same manner as that of Example 3. The ointment containing lanolin will be referred to as ointment A and that containing the esterification product (L-4) of the present invention will be referred to as ointment B. The formulations of the ointments are given in Table 8 and the results of the evaluation are given in Table 9. Table 9 shows the results of the evaluation of ointment B as compared with those of ointment A. Most of the 15 panelists concluded that ointment B containing the esterification product of the present invention was equivalent to lanolin-containing ointment A.

TABLE 8

| Starting material | Amount (% by wt.) |
|---|---|
| Sulfur | 10.0 |
| Camphor | 1.0 |
| Stearic acid | 1.0 |
| Cetanol | 4.0 |
| Isopropyl myristate | 6.0 |
| Liquid paraffin | 10.0 |
| Lanolin or L-4 | 10.0 |
| Glycerol | 8.0 |
| Polyoxyethylene-hardened castor oil | 1.0 |
| Stearic acid monoglyceride | 3.0 |
| Methylparaben | 0.2 |
| Propylparaben | 0.1 |
| Tocopherol | 0.7 |
| Purified water | 45.0 |
| Total | 100.0 |

TABLE 9

| | Evaluation of ointment | | | | | |
|---|---|---|---|---|---|---|
| | Feeling during application | | | Touch after application | | |
| | Superior | Equal | Inferior | Superior | Equal | Inferior |
| Number of panelists | 2 | 13 | 0 | 3 | 11 | 1 |

(Note)
Ointment B (containing L-4 of the present invention) was evaluated in comparison with ointment A (containing lanolin) by 15 panelists.

Example 6

Poultices containing the esterification product (L-6) of the present invention or lanolin were prepared by an ordinary method. The feeling realized during the application of them and the touch realized after the application of them were evaluated in comparison with each other in the same manner as that of Example 3. The poultice containing lanolin will be referred to as poultice A and that containing the esterification product (L-6) of the present invention will be referred to as poultice B. The formulations of the poultices are given in Table 10 and the results of the evaluation are given in Table 11. Table 11 shows the results of the evaluation of poultice B as compared with those of poultice A. Most of the 15 panelists concluded that poultice B containing the esterification product of the present invention was equivalent to lanolin-containing poultice A.

TABLE 10

| Starting material | Amount (% by wt.) |
| --- | --- |
| Kaolin | 55.0 |
| Boric acid | 5.0 |
| Conc. glycerol | 34.7 |
| Lanolin or L-5 | 5.0 |
| Thymol | 0.05 |
| Methyl salicylate | 0.2 |
| Peppermint oil | 0.05 |
| Total | 100.0 |

TABLE 11

| | Evaluation of poultice | | | | | |
| --- | --- | --- | --- | --- | --- | --- |
| | Feeling during application | | | Touch after application | | |
| | Superior | Equal | Inferior | Superior | Equal | Inferior |
| Number of panelists | 3 | 12 | 0 | 2 | 13 | 0 |

(Note)
Poultice B (containing L-6 of the present invention) was evaluated in comparison with poultice A (containing lanolin) by 15 panelists.

It was apparent from the results of the comparative tests of the creams and lipsticks, which are typical cosmetics, in Examples 3 and 4 and also from the results of the comparative tests of the ointments and poultices which are typical external preparations in Examples 5 and 6, that the esterification products of the present invention have characters and properties similar to those of lanolin.

According to the present invention, esterification products having a color, smell and stability superior to those of lanolin and an adherability, spreadability, gloss and touch very similar to those of lanolin can be obtained by esterifying glycerol with the branched fatty acid having medium chain length, long-chain linear fatty acid and dibasic acid having medium chain length under specified conditions. These esterification products can be suitably incorporated as a substitute for lanolin into products such as cosmetics, toiletries and external preparations to overcome the defects of the products due to lanolin and also to exhibit the characteristic features of the esterification products.

What is claimed is:

1. A synthetic oil produced by esterification of glycerol with a branched fatty acid selected from the group consisting of isooctylic acid and isononanoic acid, a linear fatty acid selected from the group consisting of myristic acid, stearic acid, behenic acid, and montanic acid and a dibasic acid selected from the group consisting of succinic acid, adipic acid and sebacic acid while all the following conditions (a) to (c) are satisfied:
   (a) molar ratio of the branched fatty acid to the linear fatty acid ranges from 1.7 to 2.3,
   (b) 0.7 to 0.8 mol of the dibasic acid is used per mol of glycerol, and
   (c) the number of hydroxyl groups remaining in the esterification product ranges from 0.4 to 0.6 for three hydroxyl groups of glycerol.

2. A cosmetic composition comprising the synthetic oil produced according to claim 1 and cosmetic carrier.

3. An external pharmaceutical composition comprising the synthetic oil produced according to claim 1 and a pharmaceutical carrier.

* * * * *